United States Patent [19]

Musser et al.

[11] Patent Number: 4,675,405

[45] Date of Patent: Jun. 23, 1987

[54] QUINOLINE COMPOUNDS AS ANTIALLERGIC AND ANTITHROMBOTIC AGENTS

[75] Inventors: John H. Musser, Malvern; Dennis M. Kubrak, Drexel Hill; Anthony F. Kreft, III, Devon, all of Pa.

[73] Assignee: American Home Products Corporation, New York, N.Y.

[21] Appl. No.: 823,163

[22] Filed: Jan. 27, 1986

Related U.S. Application Data

[60] Continuation-in-part of Ser. No. 787,939, Oct. 16, 1985, abandoned, which is a division of Ser. No. 653,733, Sep. 21, 1984, Pat. No. 4,581,457.

[51] Int. Cl.$^4$ .................................... C07D 215/14
[52] U.S. Cl. ............................ 546/172; 546/153; 546/157; 546/162; 546/169; 546/171; 548/483; 548/484; 548/486; 548/492; 548/504; 548/509; 548/510
[58] Field of Search .......... 546/172, 153, 157, 162, 546/169, 171; 548/483, 484, 486, 492, 504, 509, 510

[56] References Cited

PUBLICATIONS

*Chemical Abstracts*, 89:36490m (1978) [B. Cain, et al., *J. Med. Chem.*, 1978, 21(7), 658–68].

*Primary Examiner*—Richard A. Schwartz
*Attorney, Agent, or Firm*—George Tarnowski

[57] ABSTRACT

There are disclosed compounds of the formula

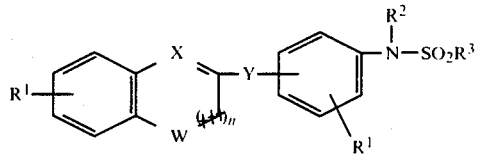

wherein
X is

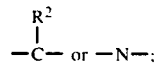

W is —O—, —S—,

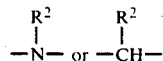

when n=0, or
W is

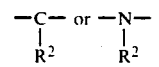

when n=1, and the dotted line represents an optional double bond;
Y is —CH$_2$O—, —OCH$_2$—, —CH$_2$S—, —SCH$_2$—,

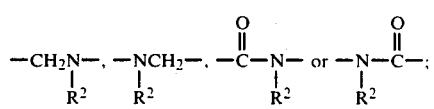

n is 0–1;
R$^1$ is hydrogen, loweralkyl, loweralkoxy, lower alkanoyl, halo, trifluoromethyl, cyano or nitro;
R$^2$ is hydrogen or loweralkyl;
R$^3$ is loweralkyl, perfluoroloweralkyl or perfluorophenyl, with the proviso that when X=N, W=O or S and n=0, R$^3$ is other than loweralkyl;
and the pharmaceutically acceptable salts thereof, and their use in the treatment of leukotriene-mediated nasobronchial obstructive airpassageway conditions, such as allergic rhinitis, allergic bronchial asthma and the like, and in antithrombotic therapy.

4 Claims, No Drawings

QUINOLINE COMPOUNDS AS ANTIALLERGIC AND ANTITHROMBOTIC AGENTS

This is a continuation-in-part of U.S. Ser. No. 787,939, filed Oct. 16, 1985, now abandoned, which is a divisional of U.S. Ser. No. 653,733, filed Sept. 21, 1984, now U.S. Pat. No. 4,581,457.

This invention relates to novel heterocyclic compounds possessing lipoxygenase inhibitory and slow-reacting substance of anaphylaxis (SRS-A) antagonist activity, which are useful as anti-inflammatory and anti-allergic agents, with some compounds also possessing the ability to inhibit thromboxane $B_2$, making them useful in antithrombotic therapy.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$). Prostacyclin is a vasodilator with platelet aggregation inhibitory activity. In the event prostacyclin synthesis is impaired and/or platelet activation is enhanced, then thromosis and vasoconstriction is favored. Abnormalities in platelet behavior and alteration in the prostacyclin/thromboxane balance have been noted in patients with diabetes mellitus [see Johnson et al., *Adv. in Prostaglandin and Thromboxane Res.*, Vol. 8, 1283 (1980)] and unstable angina pectoris [see Hirsh et al., *J. Med.*, 304, 687 (1981)]. Increases in $TxA_2$ levels have also been correlated with the severity of early post infarction arrythmias induced following acute coronary artery ligation [see Coker et al., *Nature*, 291, 323 (1981)]. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980).

With the critical role of platelets in haemostasis and thrombosis having been established, therapeutic approaches to the treatment of thrombosis, especially arterial thrombosis, are increasingly focusing on the inhibition of platelet aggregation. One of the most significant approaches to the problem is the selective inhibition of thromboxane synthetase and of antagonism of the thromboxanes. Also, since the thromboxane precursor endoperoxides will be unaffected by such a therapy, there will occur a build-up of the latter, which upon metabolism by the vascular endothelium and leukocytes, will be converted into the platelet aggregation inhibiting prostacyclin, further aiding in the inhibition of platelet aggregation. Thus, compounds which inhibit the biological effects of the thromboxanes and/or which control their biosynthesis, are considered to be of value in antithrombotic therapy.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.* 215, 115-118(1980); *Biochem. Biophys. Res. Commun.* 93, 1121-1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484-486 (1980)], and another leukotriene, $LTB_4$, is a powerful chemotactic factor for leukocytes [see A. W. Ford-Hutchinson, *J. Roy. Soc. Med.*, 74, 831-833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203-217 (1982).

The biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation must focus on either blocking the release of mediators of these conditions or to antagonize their effects. Thus, compounds which inhibit the biological effects of the leukotrienes and SRS's and/or which control the biosynthesis of these substances, as by inhibiting lipoxygenase, are considered to be of value in treating such conditions as allergic bronchial asthma, allergic rhinitis, as well as in other immediate hypersensitivity reactions.

The invention provides novel compounds of the formula

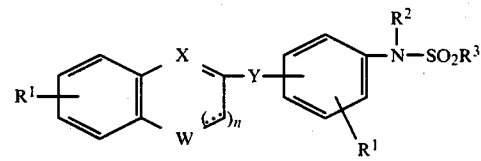

wherein
X is

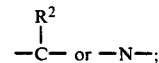

W is —O—, —S—,

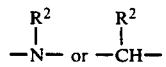

when n=0, or
W is

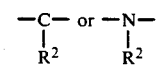

when N=1, and the dotted line represents an optional double bond;

Y is —CH$_2$O—, —OCH$_2$—, —CH$_2$S—, —SCH$_2$—,

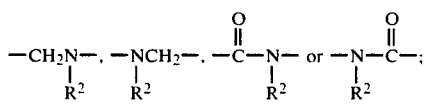

n is 0–1;

R$^1$ is hydrogen, loweralkyl, loweralkoxy, lower alkanoyl, halo, trifluoromethyl, cyano or nitro;

R$^2$ is hydrogen or loweralkyl;

R$^3$ is loweralkyl, perfluoroloweralkyl or perfluorophenyl, with the proviso that when X=N, W=O or S and n=0, R$^3$ is other than loweralkyl;

and the pharmaceutically acceptable salts thereof.

The term "halo" refers to fluoro, chloro, and bromo. The terms "loeralkyl" and "loweralkoxy" refer to moieties having 1–6 carbon atoms in the carbon chain. The term "lower alkanoyl" refers to moieties of the formula RCO— where the R radical contains 1 to 5 carbon atoms.

The compounds of the invention can be prepared by the reaction of an appropriate aniline derivative with an appropriate alkyl sulfonyl chloride or alkyl sulfonic anhydride as follows:

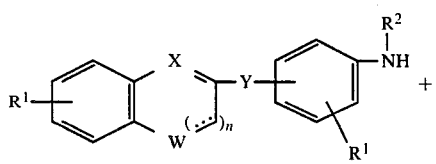

hal-SO$_2$—R$^3$ or (R$^3$SO$_2$)$_2$O ⟶

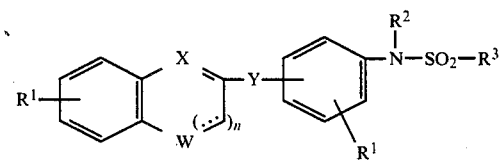

where X, W, Y, R$^1$, R$^2$, R$^3$ and n are as defined hereinbefore and hal refers to a halo radical, for example, chloro or bromo. The reaction is carried out in an organic solvent, for instance tetrahydrofuran, and at room temperatures.

The starting aniline derivatives employed in reaction sequence can be prepared as follows:

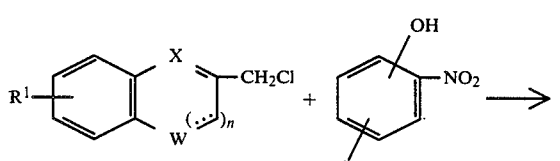

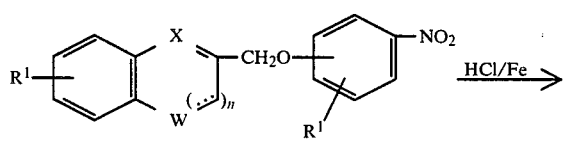

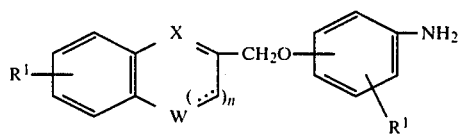

Compounds in which the bridge Y is —CH$_2$S— and —CH$_2$N— can be prepared in a like manner, using the appropriate nitrothiophenol or nitroaniline in place of the nitrophenol. Compounds in which the bridge Y is

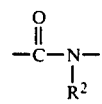

can be prepared by using the appropriate acyl chloride or acyl N-imidazole and the appropriate N-substituted nitroaniline.

The compounds of the invention having the formula

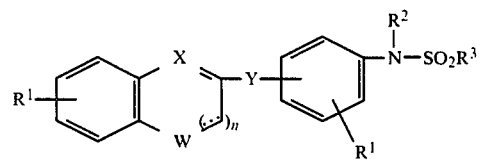

wherein R$^2$ is lower alkyl, can be readily prepared from the compounds wherein R$^2$ is hydrogen by the following reaction sequence:

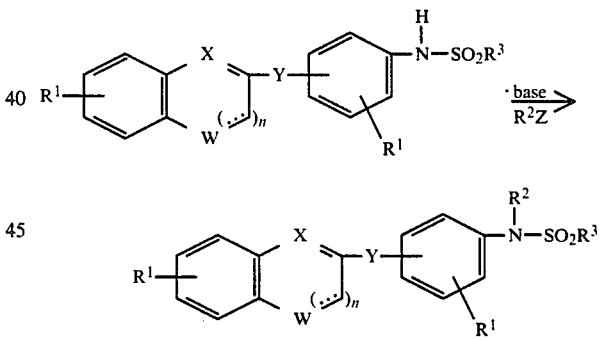

wherein W, X, Y, R$^1$, R$^2$, R$^3$ and n are as defined hereinbefore and Z is the replaceable portion of the alkylating agent R$^2$Z, which can be any of the conventional alkylating agents, such as for example the alkyl halides, alkyl sulfates, alkyl sulfonates and so forth.

Compounds of the invention which contain a basic nitrogen are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic and the like. The compounds which are carboxylic acids or have a hydroxamic function are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of the invention, by virtue of their ability to inhibit the activity of lipoxygenase enzyme and by their ability to antagonize the effects of $LTD_4$ and $LTC_4$, which are the major constituents of SRS-A, are useful for the inhibition of symptoms induced by these leukotrienes. Accordingly, the compounds are indicated in the prevention and treatment of those disease states in which $LTD_4$ and $LTC_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma. The compounds which have activity in inhibiting the synthesiss of thromboxanes and/or antagonize the effects of the thromboxanes are useful in the prevention and treatment of those conditions in which abnormal platelet aggregation induces a pathological state. Thus, such compounds are indicated in phrophylactic therapy of such thrombosis-inspired conditions as acute myocardial infarction, stroke, growth and terminal occlusion of the atherosclerotic lesion, pulmonary embolism, thromboembolism and the like.

When the compounds of the invention are employed in the treatment of allergic airways disorders or in antithrombotic therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agent and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached.

In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase inhibitory and leukotriene antagonist and the thromboxane inhibitory effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase products 5-HETE and 5,12-di-HETE; the ability of the compounds to antagonize $LTC_4$ and $LTD_4$-induced bronchospasm mediated by exogenously administered leukotrienes; measure the in vivo activity of the compounds as lipoxygenase inhibitors and leukotriene antagonists of endogenous mediators of bronchospasm, and measure the ability of the compounds to inhibit the synthesis of $TxB_2$.

The following examples show the preparation and pharmacological testing of compounds within the invention.

EXAMPLE 1

N-Ethyl-3[(2-benzothiazolyl)methoxy]phenyl sulfonamide (A) 2-chloromethylbenzothiazole To a solution of aminothiophenol (8.3 g) in methylene chloride at 0° C. is added methyl chloroacetimidate hydrochloride [prepared according to procedures described by R. Rogers and D. G. Nielson, *Chem. Rev.*, 61, 179 (1961)](8.6 g). The reaction is allowed to warm to room temperature while stirring overnight. The mixture is washed with water three times; dried over magnesium sulfate and concentrated to an oil. The oil is distilled (120°-135° C. at 0.5 mm Hg) to give 7.8 g (71% yield) of product.

(B) 3-[(2-benzothiazolyl)methoxy]nitrobenzene

A mixture of 2-chloromethylbenzothiazole (17.6 g), 3-nitrophenol (13.2 g), cesium carbonate (30 g), sodium carbonate (10 g), potassium iodide (0.5 g) and acetone (600 ml) is heated at reflux overnight. The mixture is filtered and the resulting solution is partially concentrated. A crystalline solid forms which is filtered and dried, giving 22.8 g (84% yield), m.p. 156°-157° C.

(C) 3-[(2-benzothiazolyl)methoxy]aniline

To a suspension of 3-[(2-benzothiazolyl)methoxy]nitrobenzene (18.6 g) in ethanolic hydrochloric acid is added powdered iron. The reaction is stirred overnight at room temperature. After neutralization with saturated aqueous sodium bicarbonate, the mixture is extracted three times with methylene chloride. The extract is dried over magnesium sulfate and concentrated to give 15.1 g (90% yield) of product, m.p. 117°-120° C.

(D) N-Ethyl-3-[(2-benzothiazolyl)methoxy]phenyl sulfonamide

To a solution of 3-[(2-benzothiazolyl)methoxy]aniline (2.0 g) and triethylamine (0.79 g) in tetrahydrofuran (50 ml) at room temperature is slowly added a solution of ethane sulfonyl chloride (1.0 g) in tetrahydrofuran. The reaction is stirred for 1 hour. The mixture is filtered through a pad of Celite and silica gel and the solvent is removed in vacuo giving an oil. The oil is purified by HPLC and crystallized from hexane to give 1.4 g (51% yield) of product, m.p. 111°–113° C.

Analysis for: $C_{16}H_{16}N_2O_3S_2$ Calculated: C, 55.15; H, 4.62; N, 8.03. Found: C, 55.08; H, 4.62; N, 8.14.

EXAMPLE 2

Following the procedure of Example 1 and using 2-chloromethylquinoline, 2-chloromethylnaphthalene or 2-chloromethylbenzo[b]thiophene and appropriate reagents, the following compounds are prepared:

(A) N-[3-[(2-Quinolinyl)methoxy]phenyl]ethane sulfonamide, m.p. 139°–141° C.

Analysis for: $C_{18}H_{18}N_2O_3S \cdot \frac{1}{2}H_2O$ Calculated: C, 61.52; H, 5.45; N, 7.91. Found: C, 61.32; H, 5.22; N, 7.86.

(B) N-[3-[(2-Quinolinyl)methoxy]phenyl]-1-butane sulfonamide, m.p. 89°–94° C.

Analysis for: $C_{20}H_{22}N_2O_3S \cdot \frac{3}{4}H_2O$ Calculated: C, 62.55; H, 6.17; N, 7.29. Found: C, 62.73; H, 6.02; N, 7.16.

(C) N-[3-[(2-Naphthalenyl)methoxy]phenyl]ethane sulfonamide, m.p. 131°–135° C.

Analysis for: $C_{19}H_{19}NO_3 \cdot \frac{1}{2}H_2O$ Calculated: C, 65.12; H, 5.75; N, 4.00. Found: C, 65.45; H, 5.64; N, 3.86.

(D) N-[3-[(2-Benzo[b]thienyl)methoxy]phenyl]ethane sulfonamide, m.p. 152°–154° C.

Analysis for: $C_{17}H_{17}NO_3S_2$ Calculated: C, 58.76; H, 4.93; N, 4.03. Found: C, 58.64; H, 4.59; N, 4.06.

(E) N-[3-[(2-Benzo[b]thienyl]methoxy]phenyl]-1-propane sulfonamide, m.p. 126°–128° C.

Analysis for: $C_{18}H_{19}NO_3S_2$ Calculated: C, 59.80; H, 5.29; N, 3.87. Found: C, 59.62; H, 5.22; N, 3.79.

EXAMPLE 3

N-[3-[(2-Quinolinyl)methoxy]phenyl]trifluoromethane sulfonamide

To a solution of 3-[(2-quinolinyl)methoxy]aniline (4.0 g) (prepared by following the procedures of Example 1B and 1C and using chloromethylquinoline) in methylene chloride at 0° C. is slowly added a solution of trifluoromethyl sulfonic anhydride in methylene chloride. The reaction is allowed to warm to room temperature. The mixture is filtered through celite and silica gel and concentrated to an oil. The oil is crystallized from ethanol/water to give 1.7 g (28% yield) of product, m.p. 144°–146° C.

Analysis for: $C_{17}H_{13}N_2O_3SF_3 \cdot \frac{3}{4}H_2O$ Calculated: C, 51.57; H, 3.31; N, 7.07. Found: C, 51.63; H, 3.27; N, 6.73.

EXAMPLE 4

Following the procedure of Example 1 and using appropriate starting material and reagents, the following compounds are prepared:

(A) N-Ethyl-3-[(1-methyl-2-benzimidazolyl)methoxy]phenyl sulfonamide, m.p. 169°–173° C.

Analysis for: $C_{17}H_{19}N_3O_3S$ Calculated: C, 59.11; H, 5.54; N, 12.16. Found: C, 58.87; H, 5.30; N, 12.32.

(B) N-Propyl-3-[(1-methyl-2-benzimidazolyl)methoxy]phenyl sulfonamide, m.p. 151°–153° C.

Analysis for: $C_{18}H_{21}N_3O_3S$ Calculated: C, 60.14; H, 5.88; N, 11.69. Found: C, 60.32; H, 5.76; N, 11.62.

(C) N-Butyl-3-[(1-methyl-2-benzimidazolyl)methoxy]phenyl sulfonamide, m.p. 154°–159° C.

Analysis for: $C_{19}H_{23}N_3O_3S$ Calculated: C, 59.66; H, 6.32; N, 10.98. Found: C, 59.67; H, 6.09; N, 11.17.

EXAMPLE 5

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. This is especially true with respect to 5,12-diHETE, which is also denoted as $LTB_4$ [see Ford-Hitchinson, J. Roy. Soc. Med., 74, 831 (1981)]. The assay of this Example measures the ability of the compounds of the inventin to inhibit the synthesis of 5HETE and $LTB_4$ by rat glycogen-elicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing $Ca^{++}$ and $Mg^{++}$ and 10 mM L-cysteine at a concentration of $2 \times 10^7$ cells/ml. To 1 ml portions of cell suspension, test drugs or vehicle are added and incubated at 37° C. for 10 minutes. Following this preincubation, the calcium ionophore (10 $\mu M$), A23187, is added together with 0.5 $\mu Ci$ [$^{14}C$] arachidonic acid and further incubated for 10 minutes. The reaction is stopped by the addition of ice cold water (3 ml) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are them co-chromatographed with authentic reference 5-HETE, 12-HETE and 5,12-diHETE in the solvent system—hexane:ether:acetic acid (50:50:3). After chromatography, the areas associated with 5-HETE and 5,12-diHETE standards are identified by autoradiography, cut out and quantitated by liquid scintillation.

Results are expressed as % inhibition of [$^{14}C$]5-HETE and [$^{14}C$]$LTB_4$ (5,12-HETE)synthesis.

$$\% \text{ inhibition} = \frac{\text{control} - \text{test}}{\text{control}} \times 100$$

Testing compounds of the invention in this assay and using the antioxident 3-amino-1-[m-(trifluoromethyl)-phenyl]-2-pyrazoline (BW755C) as a standard, the following results are obtained.

TABLE I

| Compound of Example Number | 50% Inhibitory Concentration ($IC_{50}$) $\mu m$ | |
|---|---|---|
| | 5-HETE | $LTB_4$ |
| BW755C | 43.0 | 30.0 |
| 2B | 1.6 | 2.1 |

Testing of other compounds of the invention in this test, but at the level of 100 $\mu m$ gives the following percentages of inhibition:

| Compound of Example Number | % Inhibition at 100 μm | |
|---|---|---|
| 2A | 93 | 85 |
| 4C | 88 | 81 |

Still other compounds of this invention are tested in this assay at a level of 50 μm, and where those compounds have an inhibition of >50%, they are designated by a "+" in the following table:

| Compound of Example Number | >50% Inhibitory at 50 μm |
|---|---|
| 2D | + |
| 2E | + |

The results shows that compounds of this invention have significant activity in inhibiting the synthesis of the arachidonic acid lipoxygenase oxidation products 5-HETE and LTB$_4$.

EXAMPLE 6

The procedure of Example 5 is also employed for the determination of the ability of the compounds of the invention to inhibit the synthesis of the arachidonic acid cyclooxygenase oxidation product TxB$_2$.

In this assay, the procedure of Example 5 is carried out as described. However, in order to determine cyclooxygenase activity, the samples are cochromatographed with authentic reference TxB$_2$ in the solvent system ethyl acetate:formic acid (80:1) and the upper phase of ethyl acetate:isoctane:acetic acid:water (110:50:20:100). After chromatography, the areas associated with TxB$_2$ standard are identified by autoradiography, cut out and quantitated by liquid scintillation techniques.

The results are calculated as in Example 5.

Testing compounds of this invention in this assay, the following results are obtained.

TABLE II

| Compound of Example Number | % Inhibition at 100 μm |
|---|---|
| 2A | 56 |
| 2B | 73 |
| 4C | 35 |

Testing other compounds of the invention in this test, at a level of 50 μm where those compounds having an inhibition of >50% are designated by a "+", gives the following results:

| Compound of Example Number | 50% Inhibition at 50 μm |
|---|---|
| 2D | + |
| 2E | + |

The results show that compounds of this invention have significant activity in inhibiting the synthesis of the arachidonic acid cyclooxygenase oxidation product TxB$_2$.

EXAMPLE 7

The assay of this Example measures the in vivo ability of the compounds of the invention to inhibit the bronchospasm induced in guinea pigs by the exogenously administered leukotrienes C$_4$ and/or D$_4$. This assay is essentially a measure of the SRS-A antagonist properties of the compounds tested.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes as described infra. Additional pentobarbital sodium (15 mg/kg, i.v.) is administered to arrest spontaneous respiration. Submaximal bronchoconstrictor responses are established in control animals by varying the dose-levels of leukotriene. Intravenous dose-levels for LTC$_4$ range from 1 to 2 μg/kg and for LTD$_4$ the range is from 0.3 to 1 μg/kg. The aerosol bronchoprovocation dose for LTC$_4$ is generated from 1.6 μM solution and for LTD$_4$ from a 2.0 μM solution.

Test drugs are administered either intravenously, intragastrically, by aerosol or orally at 1 or 10 minutes before induction of bronchospasm by administration of either LTC$_4$ or LTD$_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive saline in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

The overflow volume at 1, 3 and 5 minutes is expressed as a percentage of maximal bronchoconstriction. Combined group values are used from each of these time intervals to determine the inhibitory effect of drugs.

% inhibition =

$$\frac{\% \text{ bronchoconstriction } (bc) \text{ in control group} - \% \, bc \text{ in drug-treated groups}}{\% \, bc \text{ in control group}} \times 100$$

Students t-test for unpaired data is used to determine statistical significance. Dose reponse curves are generated and ED$_{50}$ doses are interpolated from the regression lines.

Results for compounds of the invention in this assay, using LTD$_4$ for induction of bronchospasm, are given below:

TABLE III

Compound administered at 10 minutes before induction of bronchospasm

| Compound of Example Number | Dose mg/kg (Intraduodenal) | % Inhibition (Statistical Average) Overflow Volume at | | |
|---|---|---|---|---|
| | | 1 min. | 3 min. | 5 min. |
| 2A | 50 | 88 | 86 | 81 |
| 2B | 50 | 08 | 41 | 41 |
| 2C | 50 | 61 | 41 | 53 |
| 4A | 50 | 82 | 82 | 72 |

TABLE III-continued

| Compound administered at 10 minutes before induction of bronchospasm | | | | |
|---|---|---|---|---|
| Compound of Example Number | Dose mg/kg (Intraduodenal) | % Inhibition (Statistical Average) Overflow Volume at | | |
| | | 1 min. | 3 min. | 5 min. |
| 4B | 50 | 91 | 91 | 86 |

Two other compounds of this invention are tested in this assay and the results are expressed based on the following calculations which employ the values obtained for the overflow volumes at 1, 3 and 5 minutes:

Area under the volume overflow curve (AUC) is estimated, using the overflow values at 1, 3 and 5 minutes, and expressed as a percentage of the maximal overflow AUC (equation 1):

$$\% \max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Student's t-test for unpaired data is used to determine statistical significance (p<0.05). $IC_{50}$ values can also be determined by inverse prediction from linear regression lines through points between 10 and 90% inhibition.

The results for a compound of the invention are as follows:

| Compound administered at 10 minutes before induction of bronchospasm | | |
|---|---|---|
| Compound of Example Number | Dose mg/kg (Intraduodenal) | % Inhibition of Max AUC |
| 2D | 50 | 13 |
| 4A | 50 | 72 |

The results for yet another compound of the invention are as follows:

| Compound of Example Number | Dose mg/kg | % Inhibition | $IC_{50}$ mg/kg |
|---|---|---|---|
| 3 | 25** | 98 | 0.1 |

**administered intragastrically

The results show that compounds of the invention have significant in vivo activity against $LTD_4$ induced bronchoconstriction.

EXAMPLE 8

The assay of this Example measures the in vivo ability of the compounds of the invention to inhibit the bronchospasm induced in guinea pigs by endogenous mediators of the bronchoconstriction.

The assay is carried out as follows:

Male Hartley strain guinea pigs weighing 250–350 g are sensitized to chicken ovalbumin (OA) (10 mg i.p.) on days 1 and 3 and used starting on day 26. The animals are anesthetized with pentobarbital sodium (50 mg/kg, i.p.), bilateral vagotomy is performed, and the jugular vein is cannulated for injection of drugs and the carotid artery for monitoring blood pressure. The trachea is cannulated for artificial ventilation by miniature Starling pump and for indirect measurement of respiratory volume changes as described, infra. Succinylcholine (2 mg/kg, i.v.) is administered to arrest spontaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs (dissolved in propylene glycol, polyethylene glycol or saline) are administered either intraduodenally, intragastrically or by aerosol at 2 or 10 minutes before antigen challenge. Anaphylactic bronchoconstriction is induced by administration by breaths of aerosolized OA (1%) or by intravenous administration of 0.1–0.3 mg/kg OA in saline. Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Students t-test for unpaired data is used to determine statistical significance. Dose response curves are generated and $ED_{50}$ doses are interpolated from the regression lines.

The results for a compound of the invention is this assay, using $LTD_4$ for induction of bronchospasm, are given below:

TABLE IV

| Compound administered at 10 minutes before intravenously administered ovalbumin challenge | | | |
|---|---|---|---|
| Compound of Example Number | Dose mg/kg (Intragastric) | % Inhibiton | $IC_{50}$ mg/kg |
| 3 | 25 | 97 | 0.6 |
| 4B | 50 | 74 | |

The results show that the compound tested has very significant in vivo activity in inhibiting ovalbumin induced bronchospasm mediated by endogenous products of the lipoxygenase oxidation of arachidonic acid.

What is claimed is:

1. A compound having the formula

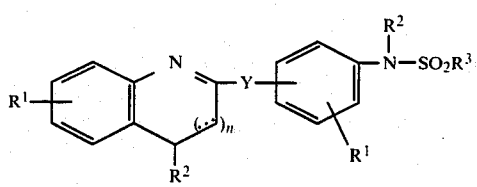

wherein

Y is —CH$_2$O—, —OCH$_2$—, —CH$_2$S—, —SCH$_2$—,

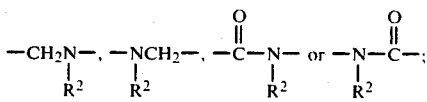

n is 0–1;
R$^1$ is hydrogen, loweralkyl, loweralkoxy, lower alkanoyl, halo, trifluoromethyl, cyano or nitro;
R$^2$ is hydrogen or loweralkyl;
R$^3$ is loweralkyl, perfluoroloweralkyl or perfluorophenyl;
or a pharmaceutically acceptable salt thereof.

2. The compound of claim 1, which is N-[3-[(2-quinolinyl)methoxy]phenyl]ethane sulfonamide.

3. The compound of claim 1, which is N-[3-[(2-quinolinyl)methoxy]phenyl]-1-butanesulfonamide.

4. The compound of claim 1, which is N-[3-[(2-quinolinyl)methoxy]phenyl]trifluoromethane sulfonamide.

* * * * *